(12) United States Patent
Wang

(10) Patent No.: US 11,773,427 B2
(45) Date of Patent: Oct. 3, 2023

(54) METHODS AND COMPOSITIONS FOR SELECTIVE CLEAVAGE OF NUCLEIC ACIDS WITH RECOMBINANT NUCLEASES

(71) Applicant: Illumina, Inc., San Diego, CA (US)

(72) Inventor: Clifford Lee Wang, Redwood City, CA (US)

(73) Assignee: Illumina, Inc., San Diego, CA (US)

( * ) Notice: Subject to any disclaimer, the term of this patent is extended or adjusted under 35 U.S.C. 154(b) by 192 days.

(21) Appl. No.: 16/609,705

(22) PCT Filed: Mar. 15, 2019

(86) PCT No.: PCT/US2019/022459
§ 371 (c)(1),
(2) Date: Oct. 30, 2019

(87) PCT Pub. No.: WO2019/182891
PCT Pub. Date: Sep. 26, 2019

(65) Prior Publication Data
US 2021/0324444 A1    Oct. 21, 2021

Related U.S. Application Data

(60) Provisional application No. 62/644,697, filed on Mar. 19, 2018.

(51) Int. Cl.
*C12Q 1/6806* (2018.01)
*C12N 15/66* (2006.01)
*C12P 21/00* (2006.01)
*C12Q 1/6874* (2018.01)

(52) U.S. Cl.
CPC .......... *C12Q 1/6806* (2013.01); *C12N 15/66* (2013.01); *C12P 21/00* (2013.01); *C12Q 1/6874* (2013.01)

(58) Field of Classification Search
None
See application file for complete search history.

(56) References Cited

U.S. PATENT DOCUMENTS 6,444,421 B1    9/2002    Chung
2007/0009937 A1*  1/2007  Laemmli .............. C12Q 1/6827
                                                            435/6.12
2010/0105049 A1   4/2010   Ehrich et al.
2013/0337460 A1   12/2013  Forsyth
2016/0272963 A1   9/2016   Forsyth
2017/0016048 A1   1/2017   Blauwkamp
2017/0218349 A1   8/2017   Miller et al.
2021/0054416 A1*  2/2021   Liu ......................... C12N 9/22

FOREIGN PATENT DOCUMENTS

WO    WO 2016/100955    6/2016

OTHER PUBLICATIONS

Fomenkov et al. Analytical BioChemistry vol. 381, No. 1, pp. 135-141, 2008 (Year: 2008).*
Shigemori, Specific cleavage of DNA molecules at RecA-mediated triple-strand structure, Nucleic Acids Research 32(1):1-8 (2004).
Duckett, et al: "Binding of the junction-resolving enzyme bacteriophage T7 endonuclease I to DNA: separation of binding and catalysis by mutation," Journal of Molecular Biology, Feb. 1995, 246(1):95-107.
Feehery, et al: "A method for selectively enriching microbial DNA from contaminating vertebrate host DNA," PLOS One, Oct. 2013, 8(10):e76096.
Fomenkov, et al: "Targeting DNA 5mCpG sites with chimeric endonucleases," Analytical Biochemistry, Oct. 2008, 381(1):135-141.

* cited by examiner

*Primary Examiner* — Jana A Hines
*Assistant Examiner* — Khatol S Shahnan Shah
(74) *Attorney, Agent, or Firm* — Knobbe, Martens, Olson & Bear LLP

(57) ABSTRACT

Some embodiments of the methods and compositions provided herein relate to the selective cleavage of a target nucleic acid. Some such embodiments include the selective cleavage of a target nucleic acid that is associated with a DNA-binding protein or comprises a methylated CpG island, with a recombinant nuclease. In some embodiments, the DNA-binding protein comprises a chromatin protein. Some embodiments also include the enrichment of non-target nucleic acids in a sample by selective cleavage of target nucleic acids in the sample, and removal of the cleaved target nucleic acids from the sample.

18 Claims, 10 Drawing Sheets
Specification includes a Sequence Listing.

METHODS AND COMPOSITIONS FOR SELECTIVE CLEAVAGE OF NUCLEIC ACIDS WITH RECOMBINANT NUCLEASES

CROSS-REFERENCE TO RELATED APPLICATIONS

This application is the U.S. National Phase of International App. No. PCT/US2019/022459 filed Mar. 15, 2019 and published in English as WO 2019/182891 on Sep. 26, 2019 which claims priority to U.S. Prov. App. No. 62/644697 filed Mar. 19, 2018 entitled "METHODS AND COMPOSITIONS FOR SELECTIVE CLEAVAGE OF NUCLEIC ACIDS WITH RECOMBINANT NUCLEASES" which are each incorporated by reference herein in its entirety.

REFERENCE TO SEQUENCE LISTING

The present application is being filed along with a Sequence Listing in electronic format. The Sequence Listing is provided as a file entitled ILLINC407WOSEQLISTING, created Mar. 13, 2019, which is approximately 13 Kb in size. The information in the electronic format of the Sequence Listing is incorporated herein by reference in its entirety.

FIELD OF THE INVENTION

Some embodiments of the methods and compositions provided herein relate to the selective cleavage of a target nucleic acid. Some such embodiments include the selective cleavage of a target nucleic acid that is associated with a DNA-binding protein or comprises a methylated CpG island, with a recombinant nuclease. In some embodiments, the DNA-binding protein comprises a chromatin protein. Some embodiments also include the enrichment of non-target nucleic acids in a sample by selective cleavage of target nucleic acids in the sample, and removal of the cleaved target nucleic acids from the sample.

BACKGROUND OF THE INVENTION

Next generation sequencing technologies are available for fast and economical determination of a genome's entire sequence. DNA and RNA sequencing can be applied for detecting pathogens and diagnosing infectious diseases.

An application of next generation sequencing is performing unbiased DNA sequencing where the sample is not enriched based on prior knowledge of sequences. Without enrichment, sequencing patient samples can yield an overwhelming majority of human sequences and a minority pathogen sequences, and the sensitivity of detection may be too low to detect low-level pathogens.

SUMMARY OF THE INVENTION

Some embodiments include a method of selectively cleaving host DNA comprising: (a) obtaining a sample comprising host DNA, wherein the host DNA is associated with a DNA-binding protein or comprises a methylated CpG; and (b) selectively cleaving the host DNA by contacting the sample with a recombinant protein comprising: a binding domain that selectively binds to the DNA-binding protein or a methylated CpG, and a nuclease domain having activity to cleave DNA. In some embodiments, the sample comprises non-host nucleic acids. Some embodiments also include (c) removing the cleaved host DNA from the non-host nucleic acids. In some embodiments, the non-host nucleic acids are not bound with the DNA-binding protein.

In some embodiments, the DNA-binding protein comprises a chromatin protein. In some embodiments, the DNA-binding protein comprises a histone. In some embodiments, the binding domain selectively binds to a histone. In some embodiments, the histone is selected from the group consisting of H1, H2A, H2B, H3, and H4. In some embodiments, the binding domain comprises a RBBP4 protein or a fragment thereof.

In some embodiments, the non-host nucleic acids lack a methylated CpG. In some embodiments, the binding domain comprises a methyl-CpG-binding domain (MBD). In some embodiments, the binding domain comprises a protein selected from the group consisting of MECP2, MBD1, MBD2, and MBD4, or a fragment thereof. In some embodiments, the binding domain comprises a MBD2 protein or a fragment thereof.

Some embodiments include a method of selectively cleaving host DNA comprising: (a) obtaining a sample comprising host DNA wherein the host DNA is associated with a DNA-binding protein or comprises a methylated CpG; (b) selectively cleaving the host DNA by contacting the sample with: an antibody or fragment thereof that selectively binds to the DNA-binding protein or a methylated CpG, and a recombinant protein comprising: a binding domain that selectively binds to the antibody or fragment thereof, and a nuclease domain having activity to cleave DNA. In some embodiments, the sample comprises non-host nucleic acids. Some embodiments also include (c) removing the cleaved host DNA from the non-host nucleic acids.

In some embodiments, the DNA-binding protein comprises a chromatin protein. In some embodiments, the chromatin protein comprises a histone. In some embodiments, the non-host nucleic acids are not bound with chromatin. In some embodiments, the antibody or fragment thereof selectively binds to a histone. In some embodiments, the histone is selected from the group consisting of H1, H2A, H2B, H3, and H4.

In some embodiments, the non-host nucleic acids lack a methylated CpG. In some embodiments, the antibody or fragment thereof selectively binds to a protein comprising a methyl-CpG-binding domain (MBD). In some embodiments, the protein comprising an MBD is a protein selected from the group consisting of MECP2, MBD1, MBD2, and MBD4. In some embodiments, the protein comprising an MBD is a MBD2 protein or a fragment thereof.

In some embodiments, the binding domain comprises a protein selected from the group consisting of Protein G and Protein A, or a fragment thereof. In some embodiments, the nuclease domain comprises a non-specific endonuclease. In some embodiments, the nuclease domain comprises a protein selected from the group consisting of Fok I and Tev I, or a fragment thereof. In some embodiments, the recombinant protein comprises a linker between the binding domain and the nuclease domain.

In some embodiments, the host DNA is mammalian DNA. In some embodiments, the host DNA is human DNA. In some embodiments, the non-host nucleic acids are selected from the group consisting of eukaryotic nucleic acids, prokaryotic nucleic acids, and viral nucleic acids.

In some embodiments, (c) comprises a step selected from the group consisting of binding the non-host nucleic acids to a substrate, hybridizing the non-host nucleic acids to a capture probe, and performing gel filtration. In some embodiments, the substrate comprises solid phase reversible immobilization (SPRI) beads.

Some embodiments include a method of selectively cleaving host DNA from a sample comprising: (a) obtaining a sample comprising host DNA, wherein the host DNA is associated with a DNA-binding protein or comprises a methylated CpG island; (b) selectively cleaving the host DNA by contacting the sample with: (i) an antibody or fragment thereof that selectively binds to the DNA-binding protein or a methylated CpG island, and (ii) a recombinant protein comprising: a binding domain that selectively binds to the antibody or fragment thereof, and a first nuclease domain, and (iii) a second nuclease domain, wherein the first and second nuclease domains together have activity to cleave DNA. In some embodiments, the sample comprises non-host nucleic acids. Some embodiments also include (c) removing the cleaved host DNA from the non-host nucleic acids In some embodiments, a second recombinant protein comprises the second nuclease domain and a second binding domain, wherein the second binding domain selectively binds to the antibody or fragment thereof, the DNA-binding protein, or a methylated CpG island. In some embodiments, the DNA-binding protein comprises a chromatin protein. In some embodiments, the chromatin protein comprises a histone.

Some embodiments include a method of preparing a library of nucleic acids comprising: (a) selectively cleaving host DNA in a sample comprising the host DNA and non-host nucleic acids according to a method provided herein, and removing the cleaved host DNA from the sample; and (b) contacting the non-host nucleic acids with a library preparation reagent, thereby preparing a library of nucleic acids. In some embodiments, (a) is performed before (b). In some embodiments, (a) is performed after (b). In some embodiments, the library preparation reagent is selected from the group consisting of a transposon, a sequencing primer, and a ligase.

Some embodiments also include sequencing the library of nucleic acids.

Some embodiments include a recombinant protein comprising: a binding domain that selectively binds to a DNA-binding protein, to a methylated CpG, or to an antibody; and a nuclease domain.

In some embodiments, the DNA-binding protein comprises a chromatin protein. In some embodiments, the chromatin protein comprises a histone. In some embodiments, the binding domain selectively binds to a histone. In some embodiments, the histone is selected from the group consisting of H1, H2A, H2B, H3, and H4. In some embodiments, the binding domain comprises a RBBP4 protein or a fragment thereof.

In some embodiments, the binding domain comprises a methyl-CpG-binding domain (MBD). In some embodiments, the binding domain comprises a protein selected from the group consisting of MECP2, MBD1, MBD2, and MBD4, or a fragment thereof. In some embodiments, the binding domain comprises a MBD2 protein or a fragment thereof.

In some embodiments, the binding domain selectively binds to an antibody. In some embodiments, the binding domain comprises a protein selected from the group consisting of Protein G and Protein A, or a fragment thereof.

In some embodiments, the nuclease domain comprises a non-specific endonuclease. In some embodiments, the nuclease domain comprises a protein selected from the group consisting of Fok I and Tev I, or a fragment thereof. In some embodiments, the recombinant protein comprises a linker between the binding domain and the nuclease domain.

In some embodiments, the nuclease domain has activity to cleave DNA in combination with a second nuclease domain.

Some embodiments include a nucleic acid encoding any one of the foregoing recombinant proteins.

Some embodiments include a cell comprising the foregoing nucleic acids.

Some embodiments include a kit for selectively cleaving host DNA bound with a DNA-binding protein or host DNA bound comprising a methylated CpG, the kit comprising: (a) a recombinant protein provided herein; and (b) a reagent selected from the group consisting of: an antibody that selectively binds to a DNA-binding protein or to methylated CpG, a second recombinant protein comprising a second nuclease domain, a reagent for removing cleaved host DNA from non-host DNA, a library preparation reagent, a nucleic acid sequencing reagent, and a capture reagent for non-cleaved nucleic acids. In some embodiments, the DNA-binding protein comprises a chromatin protein. In some embodiments, the chromatin protein comprises a histone.

DETAILED DESCRIPTION

Figure 1:
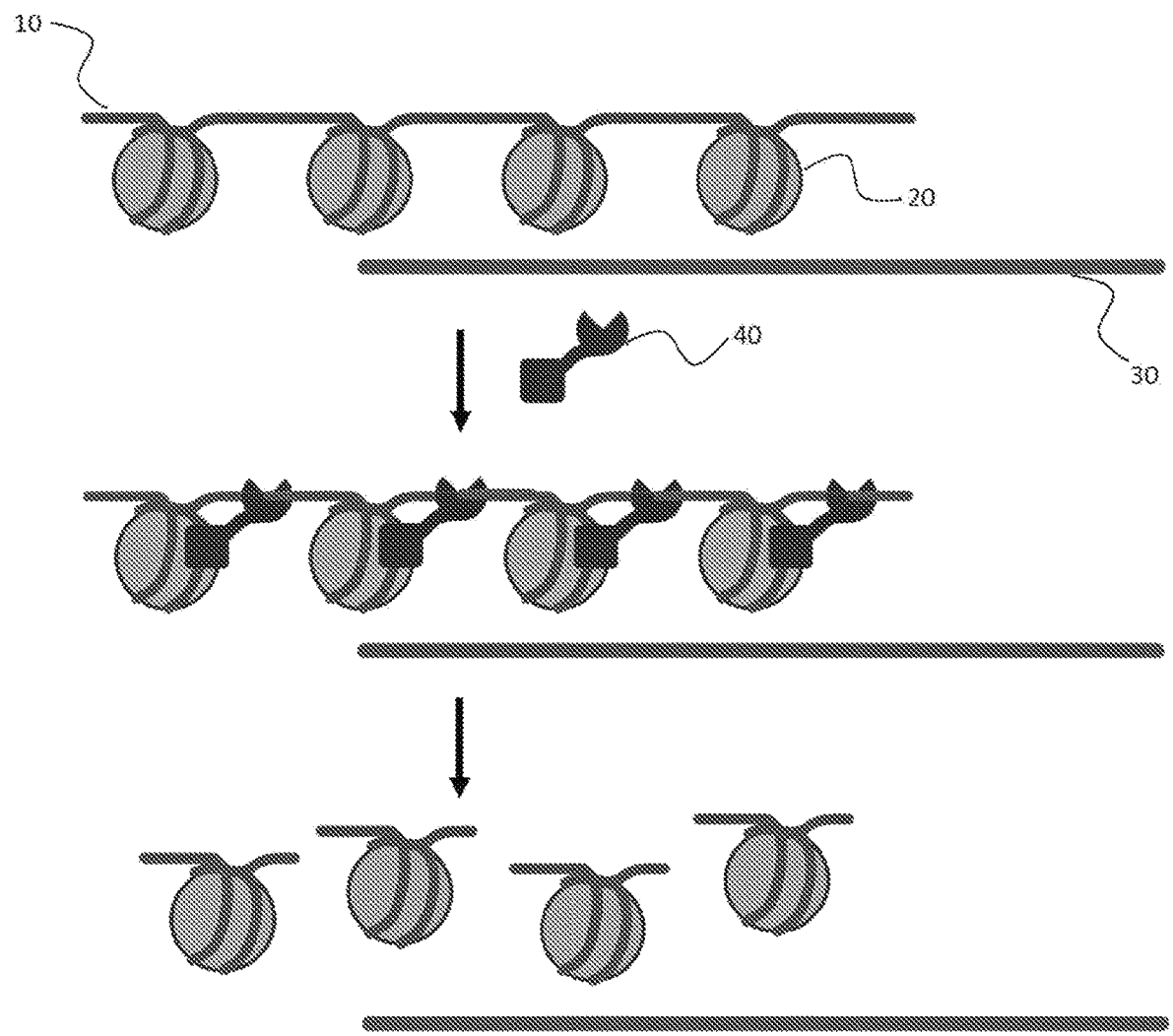
FIG. 1 depicts an embodiment in which host DNA (10) is packaged into histone complexes (20), while pathogen DNA (30) is not packed into such complexes. A recombinant enzyme (40) binds to host histone complexes, and cleaves the host DNA while leaving the pathogen DNA (30) intact.

Some embodiments of the methods and compositions provided herein relate to the selective cleavage of a target nucleic acid, such as a host DNA. Some such embodiments include the selective cleavage of a target nucleic acid, such as a host DNA that is associated with a DNA-binding protein or comprises a methylated CpG island, with a recombinant nuclease. As used herein, nucleic acids, such as host DNA, associated with a DNA-binding protein can include nucleic acids that are bound to a DNA-binding protein, such as a chromatin protein, such as a histone. Some embodiments also include the enrichment of non-target nucleic acids in a sample by selective cleavage of target nucleic acids in the sample, and removal of the cleaved target nucleic acids from the sample. Advantageously, the methods and compositions provided can be used to greatly enrich a sample of polynucleotides that includes host DNA and non-host nucleic acids, for the non-host nucleic acids, thereby increasing the sensitivity of detection of non-host nucleic acids, and reducing costs of such detection.

Some embodiments of the methods and compositions provided herein include a recombinant protein that selectively degrades host DNA. In some embodiments, the recombinant protein specifically targets features of the host DNA, such as proteins associated with the host DNA, such as host DNA-binding proteins, such as chromatin proteins, such as histones. In some embodiments, the recombinant protein specifically targets features of the host DNA such as chemical features, such as CpG methylation, or any other feature that distinguishes a host DNA from non-host nucleic acids. Embodiments of the methods and compositions provided herein are useful in, for example, applications in which non-host nucleic acids have an especially low frequency in a sample of polynucleotides comprising host DNA and non-host nucleic acids, such as pathogen detection.

The terms "polynucleotide" and "nucleic acid," may be used interchangeably herein, and refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The term "binding" refers to a direct association between two molecules, due to, for example, covalent, electrostatic, hydrophobic, and ionic and/or hydrogen-bond interactions.

Recombinant Proteins

Some embodiments of the methods and compositions provided herein relate to a recombinant protein having a binding domain that selectively binds to host DNA, and a nuclease domain having activity to cleave DNA. In some embodiments, the host DNA is associated with a DNA-binding protein, and/or comprises a methylated CpG. In some embodiments, the DNA-binding protein is a chromatin protein, such as a histone. In some embodiments, the recombinant protein is a fusion of a binding domain and a nuclease domain.

In some embodiments, the binding domain can selectively bind to a DNA-binding protein, to methylated CpG, or to an antibody. The binding domain can target the nuclease domain to the host DNA. In some embodiments, the binding domain selectively binds to a feature of the host DNA that is not associated with a non-host nucleic acid, such as a pathogen nucleic acid.

In some embodiments the binding domain selectively binds to chromatin. Chromatin includes DNA and associated histones and histone proteins. In some embodiments the binding domain selectively binds to human chromatin. In some embodiments the binding domain selectively binds to eukaryotic chromatin. In some embodiments the binding domain is a chromatin-binding domain. In some embodiments, the chromatin-binding domain selectively binds to a chromatin protein or nucleic acid.

In some embodiments the binding domain can selectively bind to a histone protein and/or a histone-binding protein. Histones are found in the nuclei of eukaryotic cells, and in certain Archaea, namely Thermoproteales and Euryarchaea, but not in bacteria or viruses. Histones are generally ubiquitous throughout eukaryotic chromosomal DNA. Eukaryotes belong to the domain Eukaryota or Eukarya, and can be unicellular or multicellular organisms. Examples of eukaryotes are organisms whose cells have a cell nucleus and other organelles enclosed within membranes, humans, animals, plants, fungi, and protozoa.

Figure 4:
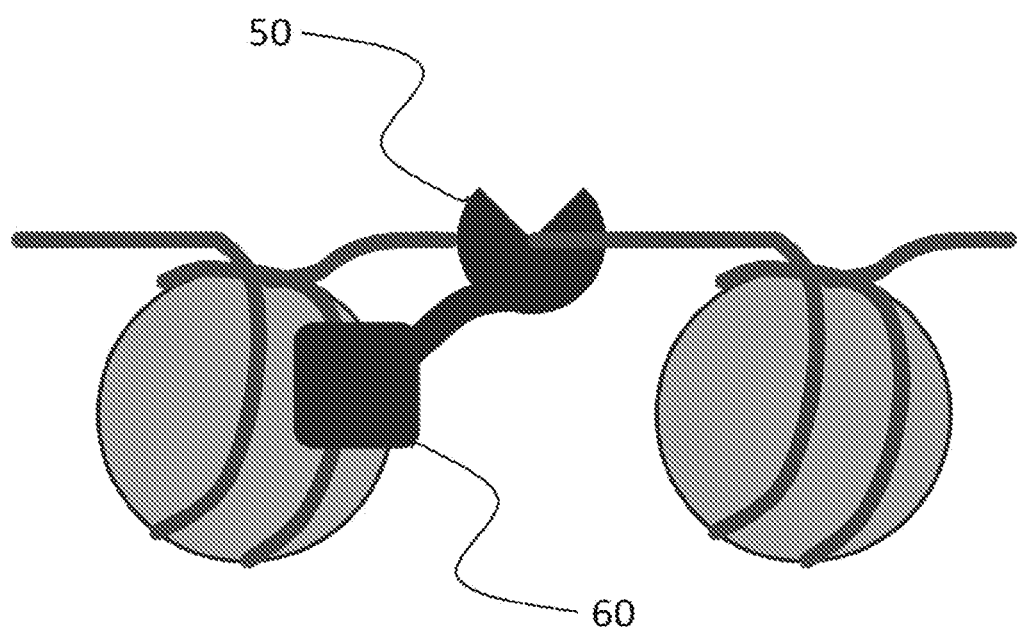
FIG. 4 depicts an embodiment of a recombinant protein that has a nuclease domain (50) and a histone-binding domain (60).

In some embodiments the binding domain selectively binds to a histone protein and DNA. FIG. 1 depicts an embodiment in which a recombinant protein (40) cleaves host DNA (10) packaged by histones into histone complexes (20), while leaving pathogen DNA (30) intact. An example of a recombinant histone nuclease containing a histone-binding domain and a nuclease domain is depicted in FIG. 4 which includes a nuclease domain (50) and a histone-binding domain (60). In some embodiments, the histone or histone protein can include a histone such as H1, H2A, H2B, H3, and H4. The histone-binding domain may bind to any histone protein or any of their variants, members, or allelic variations. A histone or histone protein may include H1, H2A, H2B, H3, or H4, or any of their variants. An example of a histone is a tetramer of two H2A-H2B dimers and a H3-H4 tetramer. A histone may comprise a linker histone: H1 or H5. Subfamily variants of H1 include H1F and H1H1. Subfamily variants of H2A include H2AF, H2A1, and H2A2. Subfamily variants of H2B include H2BF, H2B1, and H2B2J. Subfamily variants of H3 include H3A1, H3A2, and H3A3. Subfamily variants of H4 include H41 and H44. Each subfamily variant of any histone protein may include several members and/or allelic variations.

In some embodiments, the binding domain comprises a histone binding protein or a fragment thereof. In some embodiments, the binding domain comprises histone-binding protein RBBP4 (RBBP4). In some embodiments, the binding domain comprises a fragment of RBBP4.

In some embodiments, the binding domain or fragment thereof is derived from a eukaryotic organism. In some embodiments, the binding domain or fragment thereof is derived from a human. In some embodiments, the binding domain or fragment thereof is derived from an organism other than a human. In some embodiments, the binding domain is a native histone binding protein or fragment thereof. For example, the histone-binding domain of the histone nuclease can be from a native human protein. In some embodiments, the binding domain is a modified or mutated histone binding protein or fragment thereof.

In some embodiments, the histone-binding domain can include a protein domain which specifically binds to a histone such as a chromodomain, Tudor, Malignant Brain Tumor (MBT), plant homeodomain (PHD), bromodomain, SANT, YEATS, Proline-Tryptophan-Tryptophan-Proline (PWWP), Bromo Adjacent Homology (BAH), Ankryin repeat, WD40 repeat, ATRX-DNMT3A-DNMT3L (ADD), or zn-CW. In some embodiments, the histone-binding domain can include a domain which specifically binds to a histone from a protein such as HAT1, CBP/P300, PCAF/GCN5, TIP60, HB01 (ScESA1, SpMST1), ScSAS3, ScSAS2 (SpMST2), ScRTT109, SirT2 (ScSir2), SUV39H1, SUV39H2, G9a, ESET/SETDB1, EuHMTase/GLP, CLL8, SpClr4, MLL1, MLL2, MLL3, MLL4, MLL5, SET1A, SET1B, ASH1, Sc/Sp SET1, SET2 (Sc/Sp SET2), NSD1, SYMD2, DOT1, Sc/Sp DOT1, Pr-SET 7/8, SUV4 20H1, SUV420H2, SpSet 9, EZH2, RIZ1, LSD1/BHC110, JHDM1a, JHDM1b, JHDM2a, JHDM2b, JMJD2A/JHDM3A, JMJD2B, JMJD2C/GASC1, JMJD2D, CARM1, PRMT4, PRMT5, Haspin, MSK1, MSK2, CKII, Mst1, Bmi/Ring1A, RNF20/RNF40, or ScFPR4, or a histone-binding fragment thereof. In some embodiments, the binding domain can be derived from a protein associated with a histone-modifying process such as histone acetylation, deacetylation, methylation, demethylation, phosphorylation, dephosphorylation, ubiquitylation, deubiquitylation sumoylation, desumoylation, ribosylation, deribosylation, citrullination, decitrullination, imination, or deamination. In some embodiments, the binding domain binds to a DNA-binding protein, other than a histone or a protein associated with a histone.

In some embodiments, the binding domain can selectively bind to DNA comprising a methylated CpG. CG dinucleotide motifs ("CpG sites" or "CG sites") are found in regions of DNA where a cytosine nucleotide is followed by a guanine nucleotide in the linear sequence of bases along its 5' to 3' direction. CpG islands (or CG islands) are regions with a high frequency of CpG sites. CpG is shorthand for 5'-C-phosphate-G-3', that is, cytosine and guanine separated by one phosphate. Cytosines in CpG dinucleotides can be methylated to form 5-methylcytosine.

Figure 8:
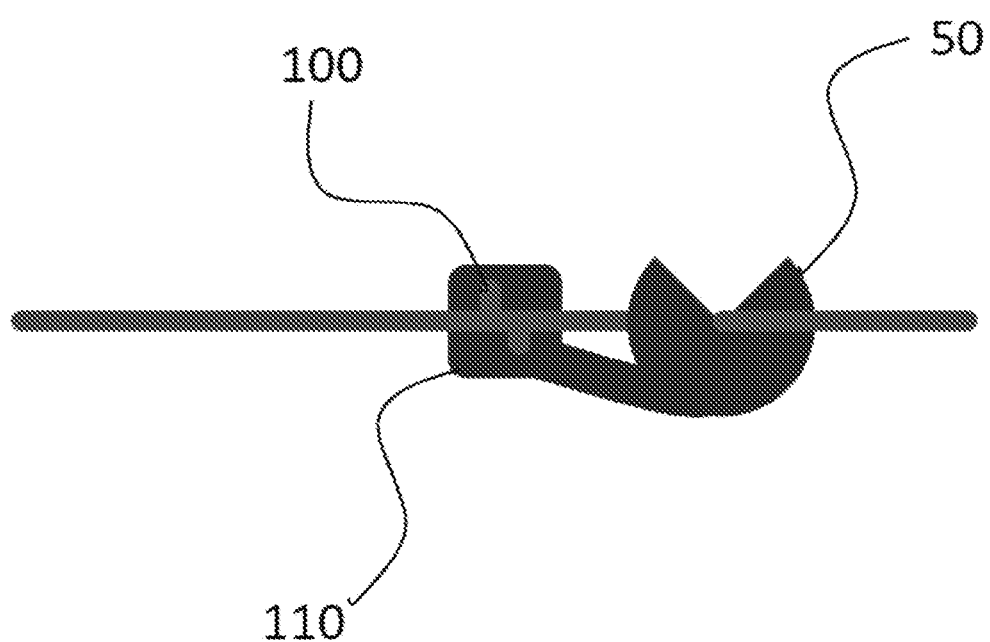
FIG. 8 depicts an embodiment in which a recombinant protein comprises a methyl-CpG-binding domain (110) and a nuclease domain (50). The methyl-CpG-binding domain is bound to methyl-CpG DNA (100).

Cytosine methylation occurs throughout the human genome at many CpG sites. Cytosine methylation at CG sites also occurs throughout the genomes of other eukaryotes. In mammals, for example, 70% to 80% of CpG cytosines may be methylated. In many pathogens of interest, such as bacteria and viruses, this CpG methylation does not occur or is significantly lower than the CpG methylation in the human genome. Thus, dehosting can be achieved by selectively cleaving CpG methylated DNA. In some embodiments, the recombinant protein is a fusion of a nuclease domain and a methyl-CpG-binding domain. An example is shown in FIG. 8 in which a recombinant protein comprises a methyl-CpG-binding domain (110) and a nuclease domain (50). The methyl-CpG-binding domain is bound to methyl-CpG DNA (100). The binding domain targets the recombinant protein to the CpG-methylated host DNA so that an associated nuclease domain can cleave it.

In some embodiments, the binding domain comprises a protein or fragment thereof that binds to CpG islands or CpG cites. In some embodiments, the binding domain comprises a protein or fragment thereof that binds to methylated CpG islands. In some embodiments, the binding domain comprises a methyl-CpG-binding domain (MBD). An example of a MBD is a polypeptide of about 70 residues that folds into an alpha/beta sandwich structure comprising a layer of twisted beta sheet, backed by another layer formed by the alpha1 helix and a hairpin loop at the C terminus. These layers are both amphipathic, with the alpha1 helix and the beta sheet lying parallel and the hydrophobic faces tightly packed against each other. The beta sheet is composed of two long inner strands (beta2 and beta3) sandwiched by two shorter outer strands (beta1 and beta4). In some embodiments, the binding domain comprises a protein selected from the group consisting of MECP2, MBD1, MBD2, and MBD4, or a fragment thereof. In some embodiments, the binding domain comprises MBD2. In some embodiments, the binding domain comprises a fragment of MBD2. In some embodiments, the binding domain comprises MBD5, MBD6, SETDB1, SETDB2, TIP5/BAZ2A, or BAZ2B, or a fragment thereof. In some embodiments, the binding domain comprises a CpG methylation or demethylation protein, or a fragment thereof.

Figure 5:
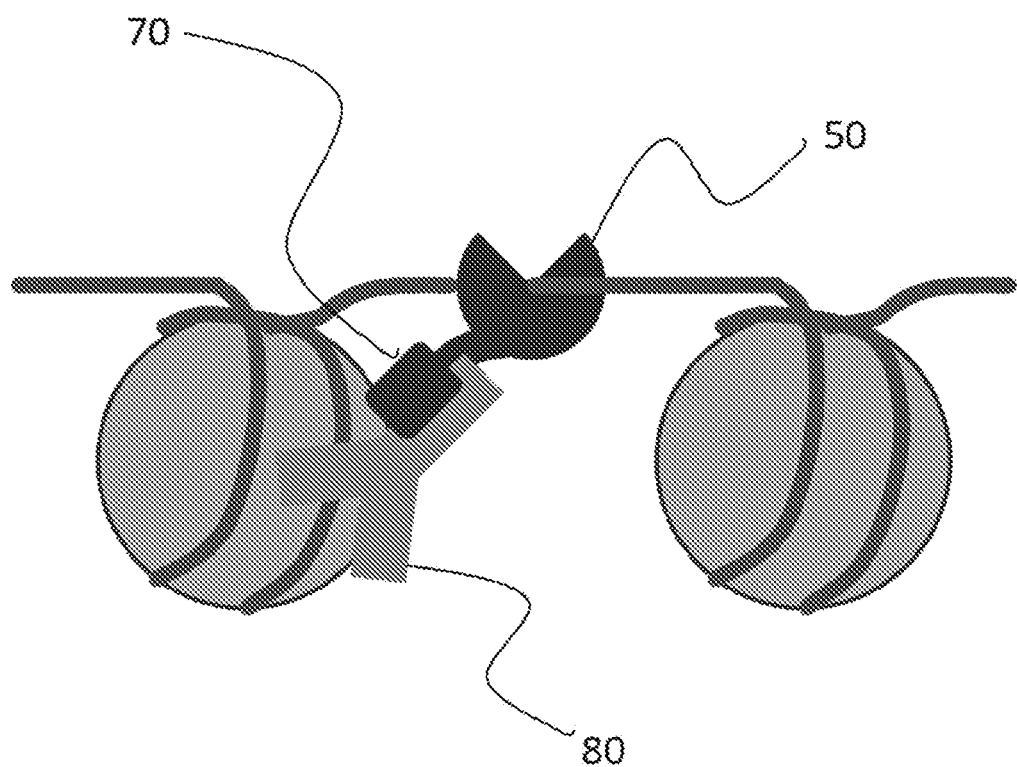
FIG. 5 depicts an embodiment of a recombinant protein that has a Protein G antibody-binding domain (70) and a nuclease domain (50). The Protein G antibody-binding domain is bound to an anti-Histone antibody (80), which is bound to a histone.
Figure 7:
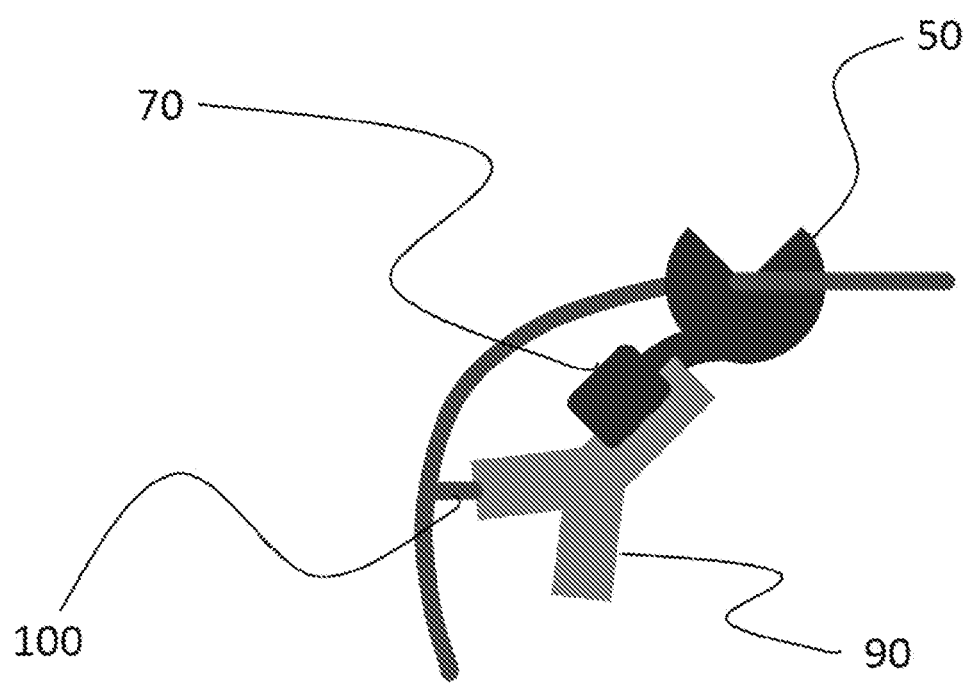
FIG. 7 depicts an embodiment in which a recombinant protein that has a Protein G antibody-binding domain (70) and a nuclease domain (50). The Protein G-binding domain is bound to an anti-5-methylcytosine antibody (90), which is bound to 5-methylcytosine (100).

In some embodiments, the binding domain can selectively bind to an antibody which selectively binds to a feature of a host DNA, such as a DNA-binding protein, or a methylated CpG. In some embodiments, the DNA-binding protein is a chromatin protein, such as histone. The nuclease domain may then be targeted to DNA proximal to the antibody. In some embodiments, the binding domain can include a domain of an antibody-binding protein which selectively binds to an antibody. In some embodiments, the antibody-binding domain binds to the Fab or Fc region of an antibody. In some embodiments, the binding domain comprises a protein selected from the group consisting of Protein G and Protein A, or a fragment thereof. In some embodiments, the Protein G or Protein A, or fragment thereof, is from a *Streptococcus*. In some embodiments, the Protein G or Protein A, or fragment thereof, binds to the Fc region of an antibody or to an Fc antibody fragment. In some embodiments, the antibody-binding domain is Protein A/G or Protein L, or a fragment thereof. As will be readily understood, some of the embodiments comprising antibodies are modular, allowing targeting of different features of host DNA depending on the antibody. An example embodiment is depicted in FIG. 5, in which a recombinant protein comprises a Protein G antibody-binding domain (70) and a nuclease domain (50). The Protein G antibody-binding domain is bound to an anti-Histone antibody (80), which is bound to a histone. Another example embodiment is depicted in FIG. 7 in which a recombinant protein comprises a Protein G antibody-binding domain (70) and a nuclease domain (50). The Protein G-binding domain is bound to an anti-5-methylcytosine antibody (90), which is bound to 5-methylcytosine (100). Some such embodiments can target regions of methylated DNA for degradation.

Antibodies against a feature of host DNA can be prepared by methods known in the art. An example of an antibody, or immunoglobulin, is a large, globular plasma protein of about 150 kDa. It may comprise, for example, four polypeptides—two heavy chains and two light chains joined to form a "Y" shaped molecule. The amino acid sequence in the tips of the "Y" may vary greatly among different antibodies. This variable region, composed of, for example, 110-130 amino acids, may give the antibody its specificity for binding an antigen. The variable region may include ends of light and heavy chains. Treating the antibody with a protease can cleave this region, producing Fab or fragment antigen binding that include the variable ends of an antibody. In some embodiments, the antibodies include class IgM, IgG, Iga, IgD, or IgE antibodies. In some embodiments, the antibodies are monoclonal. In some embodiments, the monoclonal antibodies are produced by a hybridoma cell line. In some embodiments, the antibodies are polyclonal.

In some embodiments, the binding domain comprises a fragment of an antibody which selectively binds to a feature of host DNA. In some embodiments, the binding domain comprises a fragment of an antibody that selectively binds to a particular DNA-binding protein, such as a chromatin protein. In some embodiments, the binding domain comprises a fragment of an anti-histone antibody. In some embodiments, the binding domain comprises a fragment of an anti-methyl-CpG antibody. In some embodiments, the anti-methyl-CpG antibody comprises an anti-5-methylcytosine antibody.

In some embodiments, the recombinant protein may include a second binding domain. For example, the recombinant protein may include a methyl-CpG-binding domain and a histone-binding domain, two methyl-CpG-binding domains, or two histone-binding domains. In some embodiments, including a second binding domain improves the specificity of the binding to host DNA.

In some embodiments, the nuclease domain of a recombinant protein can include a non-specific nuclease. In some embodiments, the nuclease domain is an endonuclease or a fragment thereof. In some embodiments, the nuclease domain is a non-specific endonuclease or a fragment thereof. In some embodiments, the nuclease domain is a non-specific exonuclease or a fragment thereof. In some embodiments, the nuclease domain is a homing endonuclease or a fragment thereof. In some embodiments, the nuclease domain is a restriction endonuclease or a fragment thereof. In some embodiments, the nuclease domain is a human protein, or a fragment thereof. In some embodiments, the nuclease domain is a eukaryotic protein, or a fragment thereof. In some embodiments, the nuclease domain is a non-eukaryotic protein, or a fragment thereof.

In some embodiments, the nuclease domain is derived from any nuclease where the nuclease domain does not itself have its own unique target. In some embodiments, the nuclease domain has activity when fused to other proteins. Examples of non-specific nucleases include FokI and I-TevI. In some embodiments, the nuclease domain is FokI or a fragment thereof. In some embodiments, the nuclease domain is I-TevI or a fragment thereof. In some embodiments, the FokI or I-TevI or fragment thereof is unmutated and/or wild-type.

TABLE 1 lists example FokI variants and their polypeptide sequences. In some embodiments, the FokI or a functional fragment thereof comprises a polypeptide having identity with a polypeptide selected from SEQ ID NO:01, SEQ ID NO:02, SEQ ID NO:03, SEQ ID NO:04, SEQ ID NO:05, SEQ ID NO:06, SEQ ID NO:07, SEQ ID NO:08, SEQ ID NO:09, SEQ ID NO:10, and SEQ ID NO:11 of at least 70%, 80%, 90%, 95% or 100%, or a percentage with a range of any two of the foregoing percentages, or a conservative variation of any one of the foregoing polypeptides. In some embodiments, FokI includes a dimer of any of the polypeptides identified in SEQ ID NOs:01-11. In some embodiments, the use of one or more FokI variants instead of wild-type FokI enhances the nuclease activity of the recombinant protein. In some embodiments, the nuclease domain has a mutation that renders it cold or heat sensitive.

TABLE 1

| SEQ ID NO. | FokI variant | Amino acid sequence |
|---|---|---|
| 01 | Wild-Type | QLVKSELEEKKSELRHKLKYVPHEYIELIEIARNSTQDRILEM KVMEFFMKVYGYRGKHLGGSRKPDGAIYTVGSPIDYGVIVD TKAYSGGYNLPIGQADEMQRYVEENQTRNKHINPNEWWKV YPSSVTEFKFLFVSGEIFKGNYKAQLTRLNHITNCNGAVLSVE ELLIGGEMIKAGTLTLEEVRRKFNNGEINF |
| 02 | EL | QLVKSELEEKKSELRHKLKYVPHEYIELIEIARNSTQDRILEM KVMEFFMKVYGYRGKHLGGSRKPDGAIYTVGSPIDYGVIVD TKAYSGGYNLPIGQADEMERYVEENQTRNKHLNPNEWWK VYPSSVTEFKFLFVSGHFKGNYKAQLTRLNHITNCNGAVLS VEELLIGGEMIKAGTLTLEEVRRKFNNGEINF |
| 03 | KK | QLVKSELEEKKSELRHKLKYVPHEYIELIEIARNSTQDRILEM KVMEFFMKVYGYRGKHLGGSRKPDGAIYTVGSPIDYGVIVD TRAYSGGYNLPIGQADEMQRYVKENQTRNKHINPNEWWK VYPSSVTEFKFLFVSGHFKGNYKAQLTRLNHKTNCNGAVLS VEELLIGGEMIKAGTLTLEEVRRKFNNGEINF |
| 04 | D | QLVKSELEEKKSELRHKLKYVPHEYIELIEIARNSTQDRILEM KVMEFFMKVYGYRGKHLGGSRKPDGAIYTVGSPIDYGVIVD TRAYSGGYNLPIGQADEMQDYVEENQTRNKHINPNEWWKV YPSSVTEFKFLFVSGHFKGNYKAQLTRLNHITNCNGAVLSVE ELLIGGEMIKAGTLTLEEVRRKFNNGEINF |
| 05 | R | QLVKSELEEKKSELRHKLKYVPHEYIELIEIARNSTQDRILEM KVMEFFMKVYGYRGKHLGGSRKPDGAIYTVGSPIDYGVIVD TRAYSGGYNLPIGQAREMQRYVEENQTRNKHINPNEWWKV YPSSVTEFKFLFVSGHFKGNYKAQLTRLNHITNCNGAVLSVE ELLIGGEMIKAGTLTLEEVRRKFNNGEINF |
| 06 | EA | QLVKSELEEKKSELRHKLKYVPHEYIELIEIARNSTQDRILEM KVMEFFMKVYGYRGKHLGGSRKPDGAIYTVGSPIDYGVIVD TRAYSGGYNLPIGQADEMERYVEENQTRNKHANPNEWWK VYPSSVTEFKFLFVSGHFKGNYKAQLTRLNHITNCNGAVLS VEELLIGGEMIKAGTLTLEEVRRKFNNGEINF |
| 07 | KV | QLVKSELEEKKSELRHKLKYVPHEYIELIEIARNSTQDRILEM KVMEFFMKVYGYRGKHLGGSRKPDGAIYTVGSPIDYGVIVD TRAYSGGYNLPIGQADEMQRYVKENQTRNKHINPNEWWK |

TABLE 1-continued

| SEQ ID NO. | FokI variant | Amino acid sequence |
|---|---|---|
| | | VYPSSVTEFKFLFVSGHFKGNYKAQLTRLNHVTNCNGAVLS VEELLIGGEMIKAGTLTLEEVRRKFNNGEINF |
| 08 | ELD | QLVKSELEEKKSELRHKLKYVPHEYIELIEIARNSTQDRILEM KVMEFFMKVYGYRGKHLGGSRKPDGAIYTVGSPIDYGVIVD TRAYSGGYNLPIGQADEMERYVEENQTRDKHLNPNEWWK VYPSSVTEFKFLFVSGHFKGNYKAQLTRLNHITNCNGAVLS VEELLIGGEMIKAGTLTLEEVRRKFNNGEINF |
| 09 | KKR | QLVKSELEEKKSELRHKLKYVPHEYIELIEIARNSTQDRILEM KVMEFFMKVYGYRGKHLGGSRKPDGAIYTVGSPIDYGVIVD TRAYSGGYNLPIGQADEMQRYVKENQTRNKHINPNEWWK VYPSSVTEFKFLFVSGHFKGNYKAQLTRLNRKTNCNGAVLS VEELLIGGEMIKAGTLTLEEVRRKFNNGEINF |
| 10 | Sharkey | QLVKSELEEKKSELRHKLKYVPHEYIELIEIARNPTQDRILEM KVMEFFMKVYGYRGEHLGGSRKPDGAIYTVGSPIDYGVIVD TKAYSGGYNLPIGQADEMQRYVEENQTRNKHINPNEWWKV YPSSVTEFKFLFVSGEIFKGNYKAQLTRLNHITNCNGAVLSVE ELLIGGEMIKAGTLTLEEVRRKFNNGEINF |
| 11 | Sharkey' | QLVKSELEEKKSELRHKLKYVPHEYIELIEIARNPTQDRILEM KVMEFLMKVYGYRGEHLGGSRKPDGAIYTVGSPIDYGVIVD TKAYSGGYNLPIGHADEMQRYVEENQTRNKHINPNEWWKV YPSSVTEFKFLFVSGYFKGDYKAQLTRLNHITNCNGAVLSVE ELLIGGEMIQAGTLTLEEVRRKFNNGEINF |

Figure 6:
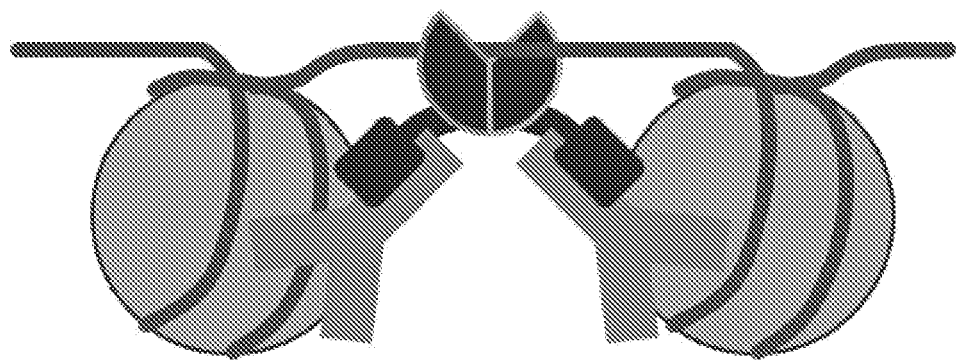
FIG. 6 depicts an embodiment in which a recombinant protein that has a heterodimeric nuclease domain, and two antibody-binding domains. The two antibody-binding domains are each bound to a different kind of anti-histone antibody.

In some embodiments, the nuclease domain has activity to cleave DNA in combination with a second nuclease domain. In some embodiments, the nuclease domain is a homodimer. In some embodiments, the nuclease domain is a heterodimer. For example, in some embodiments, specificity can be increased by using a split, heterodimeric nuclease domain (FIG. 6). The second heterodimer subunit can be used as another fusion (pictured in FIG. 6) or added alone (not fused to a nuclease domain) after initial binding of the nuclease.

In some embodiments, the nuclease domain is Deoxyribonuclease I (DNase I), RecBCD enonuclease, T7 endonuclease, T4 endonuclease IV, Bal 31 endonuclease, Endonucleasel (endo I), Micrococcal nuclease, Endonuclease II (endo VI, exo III), Neurospora endonuclease, S1-nuclease, P1-nuclease, Mung bean nuclease I, Ustilago nuclease (Dnase I), AP endonuclease, or Endo R, or a fragment thereof.

In some embodiments, the nuclease domain comprises a polypeptide having identity with a polypeptide selected from SEQ ID NOs:01-11, of at least 70%, 80%, 90%, 95%, 99% or 100%, a functional fragment thereof, or a conservative variation of any one of the foregoing polypeptides. In some embodiments, a conservative amino acid variation can include an amino acid substitution that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups, for example, replacement of phenylalanine with the smaller isoleucine. Families of amino acid residues having similar side chains have been defined in the art. Several families of conservative amino acid substitutions are shown in TABLE 2.

TABLE 2

| Family | Amino Acids |
|---|---|
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| beta-branched | Thr, Val, Ile |
| residues that influence chain orientation | Gly, Pro |
| aromatic | Trp, Tyr, Phe, His |

In some embodiments, the recombinant protein comprises a linker between the binding domain and the nuclease domain. In some embodiments, the linker directly connects the binding domain and the nuclease domain. The linker can be flexible or rigid, long or short, native or synthetic. TABLE 3 lists examples of binding domains, linkers, and nuclease domains that the recombinant protein can include in various permutations.

TABLE 3

| Example binding domains | Example linkers | Example nuclease domains |
|---|---|---|
| Histone binding protein RBBP4 | Flexible/Rigid | Fold nuclease domain |
| Antibody binding Protein G Antibody binding Protein A Monoclonal/polyclonal Antibodies | Native/synthetic Long/short | I-TevI nuclease domain |

In some embodiments, the recombinant protein comprises a detectable label. Examples of detectable labels include, for example, biotin, glutathione S-transferase (GST), polyhistidine (HIS), and digioxigenin.

In some embodiments, the protein is purified or substantially purified. In some embodiments, the protein is purified or substantially purified using a detectable label. The recombinant proteins described above may be referred to as "recombinant nucleases," "recombinant enzymes," "engineered nucleases," and "engineered enzymes." Some embodiments provided herein relate to a nucleic acid encoding any of the recombinant proteins described above. In some embodiments, the nucleic acid is encoded within a vector. In some embodiments, the vector is a cloning vector or an expression vector. Examples of vectors include human or animal viruses such as vaccinia virus or adenovirus; insect viruses such as baculovirus; yeast vectors; bacteriophage vectors (e.g., lambda), and plasmid and cosmid DNA vectors, to name a few. In some embodiments, the vector includes a selectable marker. Such markers may allow identification and/or selection of host cells that incorporate and express the proteins encoded by the marker. In some embodiments, the vector includes a promoter element, for directing transcription of a gene. Some embodiments provided herein relate to a cell comprising the nucleic acid or recombinant protein described above. In some embodiments, the nucleic acid is stably expressed by the cell. In some embodiments, the nucleic acid is integrated into the genome of the cell. In some embodiments, the nucleic acid is transiently expressed.

Selective Cleavage of Host DNA

Some embodiments provided herein relate to a method of selectively cleaving host DNA using a recombinant protein provided herein. Some embodiments include obtaining a sample comprising host DNA in which the host DNA is associated with a DNA-binding protein, or comprises a methylated CpG. In some embodiments, the DNA-binding protein is a chromatin protein, such as a histone. The sample can be contacted with the recombinant protein, thereby selectively cleaving the host DNA. Some embodiments include selectively cleaving a host DNA with a recombinant protein provided herein and an antibody or fragment thereof that selectively binds to a feature of the host DNA, such as a DNA-binding protein or a methylated CpG. In some such embodiments, the antibody binds to a feature of the host DNA, the recombinant protein binds to the antibody and cleaves the host DNA Some embodiments also include dehosting a sample of polynucleotides comprising host DNA and non-host nucleic acids. Some such embodiments include selectively cleaving the host DNA, and removing the cleaved host DNA from the non-host nucleic acids.

In some embodiments, a sample can be obtained from a cell, fluid, tissue, or organ from an organism or cell-culture, such as blood, serum, plasma, tears, saliva, mucus, urine, milk, semen, muscle, heart, liver, skin, liver, kidney, or adipose tissue. In some embodiments, a sample can be from a cell-culture. In some embodiments, a sample is an environmental sample, such as a soil, water, or air sample. In some embodiments, the sample is a biological sample. In some embodiments, the sample is from a human. In some embodiments, the sample is from a non-human eukaryote. In some embodiments, the sample is from an animal. In some embodiments, the sample is from a plant. In some embodiments, the sample is from a fungus. In some embodiments, the sample is from a protozoan. In some embodiments, the sample contains nucleic acid from at least two different prokaryotic organisms. In some embodiments, the sample contains nucleic acid from human and bacterial organisms. In some embodiments, the sample contains nucleic acid from eukaryotic and prokaryotic organisms. In some embodiments, the sample contains nucleic acid from at least two different eukaryotic organisms. In some embodiments, the sample contains nucleic acid from an unknown organism.

In some embodiments, the sample contains, for example, less than 10 pg, less than 9 pg, less than 8 pg, less than 7 pg, less than 6 pg, less than 5 pg, less than 4 pg, less than 3 pg, less than 2 pg, or less than 1 pg of non-host nucleic acids, or any range of values thereof. In some embodiments, the sample contains, for example, from 10 pg to 1 pg, from 9 pg to 1 pg, from 8 pg to 1 pg, from 7 pg to 1 pg, from 6 pg to 1 pg, from 5 pg to 1 pg, from 4 pg to 1 pg, from 3 pg to 1 pg, or from 2 pg to 1 pg of non-host nucleic acids.

In some embodiments, host DNA is bound with a protein, such as a chromatin protein, such as a histone. In some embodiments, host DNA comprises an epigenetic modification, such as a methylated CpG. In some embodiments, the host DNA is eukaryotic, such as mammalian, such as human. In some embodiments, the host DNA is non-human DNA. The host DNA can include double-stranded DNA, and/or single-stranded DNA. In some embodiments, the host DNA is chromatin, and the non-host nucleic acids are non-chromatin nucleic acids. In some embodiments, the host DNA includes histones or histone proteins. In some embodiments, the histone proteins of the host DNA are selected from the group consisting of H1, H2A, H2B, H3, and H4. In some embodiments, the binding domain of the recombinant protein selectively binds to a histone. In some embodiments, the binding domain of the recombinant protein comprises a RBBP4 protein or a fragment thereof.

In some embodiments, the non-host nucleic acids can include nucleic acids that are not bound with the DNA-binding protein that can be associated with the host nucleic acids. In some embodiments, the DNA-binding protein is a chromatin protein, such as a histone. In some embodiments, the non-host nucleic acids can include nucleic acids that lack a methylated CpG. In some embodiments, non-host nucleic acids do not include a binding partner or are not bound to a binding partner which is selectively bound by a binding domain of a recombinant protein provided herein. In some embodiments, non-host nucleic acids do not include a binding partner or are not bound to a binding partner which is selectively bound by an antibody which is selectively bound by a binding domain of a recombinant protein provided herein. In some embodiments, non-host nucleic acids can comprise eukaryotic, prokaryotic nucleic acids, or viral nucleic acids. In some embodiments, the non-host nucleic acids are archaic nucleic acids. Non-host nucleic acids can include DNA, and RNA.

Some embodiments include extracting host DNA from a sample. In some such embodiments, DNA can be extracted from the sample such that associated proteins, such as certain DNA-binding proteins such as histones, remain associated with the extracted DNA. In some embodiments, keeping certain DNA-binding proteins such as histones associated with the extracted DNA can include excluding proteases during DNA extraction, using a gentle wash step, using a buffer formulated to keep histones intact, avoiding harsh reagents and detergents that interfere with the non-covalent bonds between the DNA-binding proteins and DNA, or extracting DNA without precipitating the DNA. In some embodiments, the method includes treating the sample with a protease inhibitor.

Some embodiments include removing cleaved host DNA from non-host nucleic acids. In some such embodiments, cleaved host DNA can be removed from non-host nucleic acids based on differences in the average size of the cleaved host DNA fragments, and the non-host nucleic acids. In some embodiments, removing cleaved host DNA from the non-host nucleic acids comprises removing nucleic acids of less than 1000 bases or base pairs. In some embodiments, removing cleaved host DNA from the non-host nucleic acids comprises removing nucleic acids of less than 500 bases or base pairs. In some embodiments, removing cleaved host DNA from the non-host nucleic acids comprises removing nucleic acids of less than 400 bases or base pairs. In some embodiments, removing cleaved host DNA from the non-host nucleic acids comprises removing nucleic acids of less than 300 bases or base pairs. In some embodiments, removing cleaved host DNA from the non-host nucleic acids comprises removing nucleic acids of less than 200 bases or base pairs. In some embodiments, removing cleaved host DNA from the non-host nucleic acids comprises removing nucleic acids of less than 100 bases or base pairs. In some embodiments, removing cleaved host DNA from the non-host nucleic acids comprises removing nucleic acids of less than 2000 bases or base pairs.

In some embodiments, removing cleaved host DNA from the non-host nucleic acids comprises binding the non-host nucleic acids to a substrate, hybridizing the non-host nucleic acids to a capture probe, or performing gel filtration. In some embodiments, the substrate comprises solid phase reversible immobilization (SPRI) beads. In some embodiments, the substrate comprises a solid substrate such as, for example, a magnetic bead, a microtiter plate well, and a column surface.

Some embodiments provided herein relate to a method of removing host DNA from a sample comprising: (a) obtaining a sample comprising host DNA and non-host nucleic acids; (b) selectively cleaving the host DNA by contacting the sample with: (i) an antibody or fragment thereof that selectively binds to host DNA, and a recombinant protein comprising: a binding domain that selectively binds to the antibody or fragment thereof, and a first nuclease domain, and (ii) a second nuclease domain, wherein the first and second nuclease domains together have activity to cleave DNA; and (c) removing the cleaved host DNA from the non-host nucleic acids. In some embodiments, the first and second nuclease domains form a dimer. In some embodiments, a second recombinant protein comprises the second nuclease domain and a second binding domain, wherein the second binding domain selectively binds to the antibody or fragment thereof, or selectively binds to host DNA.

Preparation of Nucleic Acid Libraries

Figure 2:
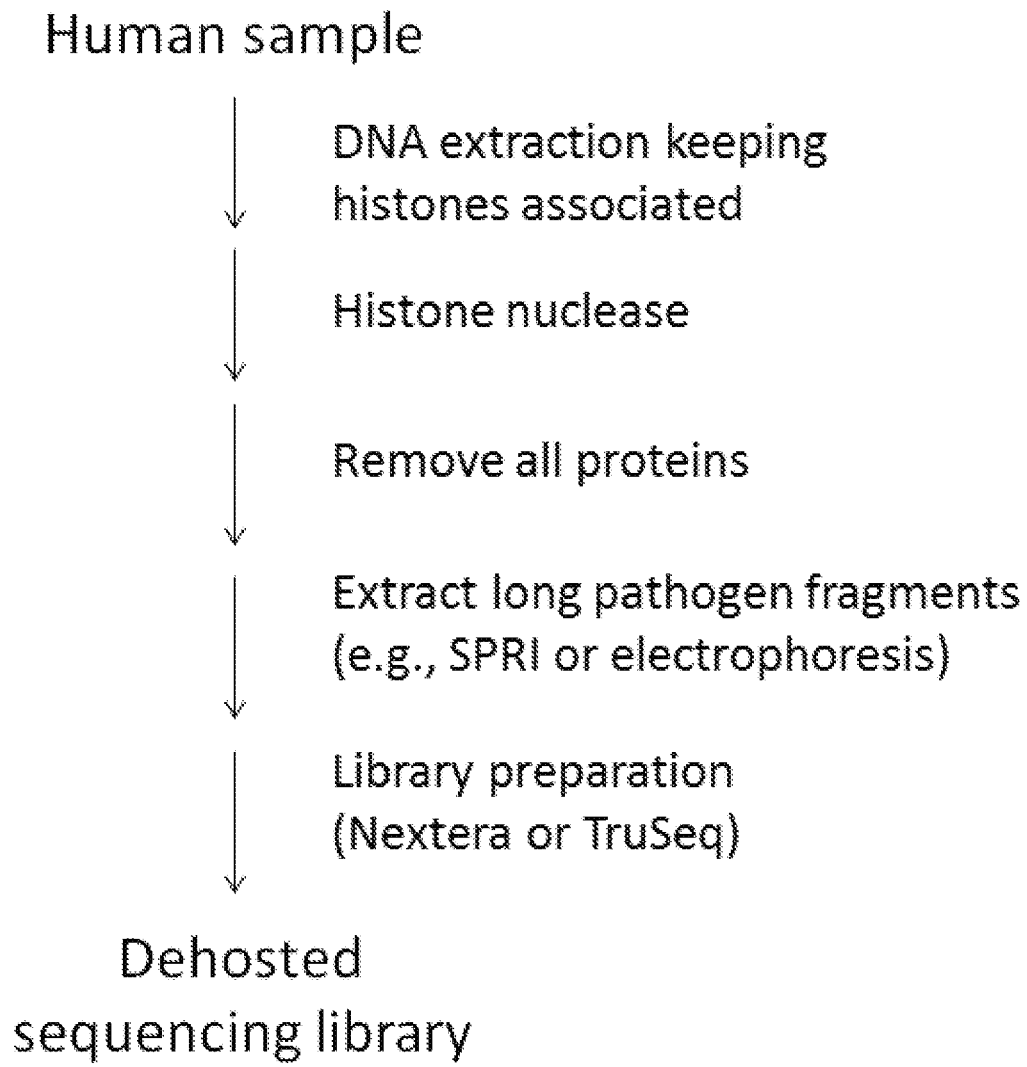
FIG. 2 depicts an embodiment in which a histone nuclease is used to cleave human DNA in a human sample and remaining pathogen nucleic acids are used to prepare a library for sequencing.

Some embodiments provided herein relate preparing a library of nucleic acids. In some embodiments, a library preparation reagent can include a transposon, a sequencing primer, or a ligase. In some embodiments, the library of nucleic acids can be sequenced. Some embodiments can include selectively cleaving a host DNA in a sample of polynucleotides comprising the host DNA and non-host nucleic acids. The non-host nucleic acids can be removed from the cleaved host DNA, and used to prepare a library of nucleic acids. An example embodiment is depicted in FIG. 2. In FIG. 2, a recombinant protein such as a histone nuclease can be used to dehost samples before library preparation. For example, a human sample is provided; DNA extraction is performed keeping histones associated; a histone nuclease described above is added to the extracted DNA; proteins (including the histone nuclease) are then removed by, for example, adding a protease or precipitating the DNA; pathogen nucleic acids are then extracted and separated from shorter cleaved host DNA fragments by, for example, SPRI or electrophoresis and gel purification; then a sequencing library is prepared by, for example, using NEXTERA® or TRUSEQ® technology (Illumina, Inc, San Diego, CA), resulting in a dehosted sequencing library that may, for example, be subjected to unbiased sequencing to identify non-host and/or pathogen nucleic acids that were in the initial human sample. In another embodiment, the recombinant protein can be a methyl-CpG nuclease.

Figure 3:
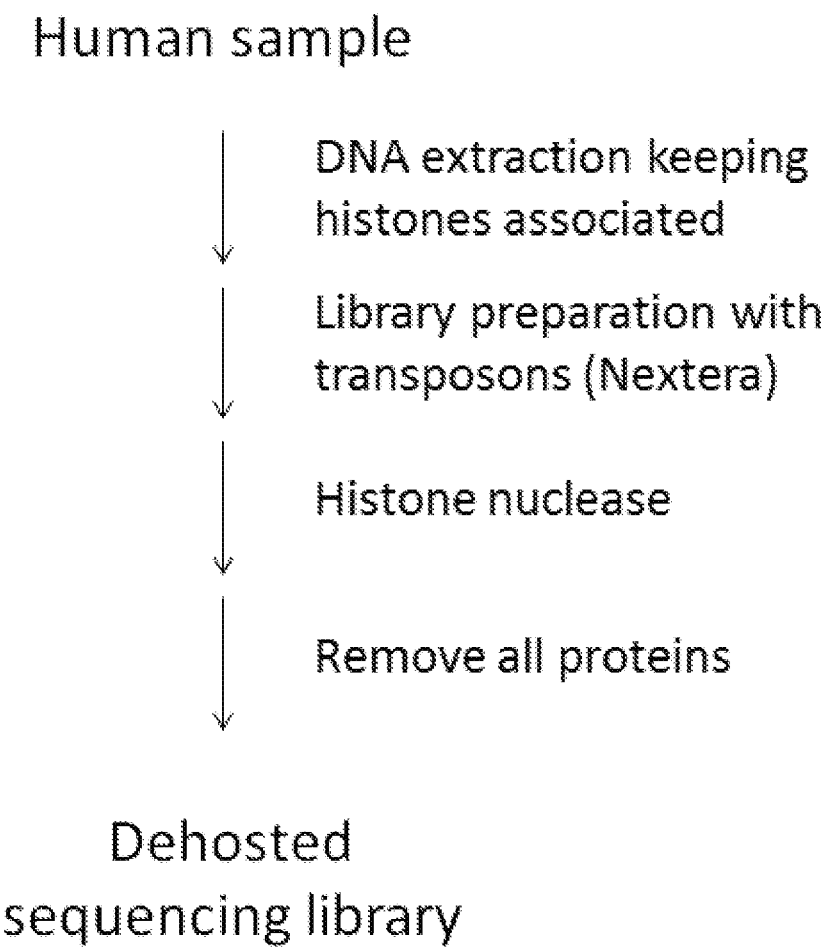
FIG. 3 depicts an embodiment in which a library of nucleic acids is prepared from a human sample, and a histone nuclease is used to cleave human DNA from the library.

In some embodiments, a library of nucleic acids can be prepared from a sample of polynucleotides comprising host DNA and non-host nucleic acids, and host DNA subsequently removed from the library of nucleic acids by selectively cleaving the host DNA using recombinant proteins provided herein. An example embodiment is depicted in FIG. 3, in which a recombinant protein such as a histone nuclease can be used to dehost samples after library preparation. For example, a human sample is provided; DNA extraction is performed keeping histones associated; a sequencing library is prepared by, for example, using NEXTERA® technology; then a histone nuclease described above is added to the library; proteins (including the histone nuclease) are then removed by, for example, adding a protease or precipitating the DNA; at some point after histone nuclease treatment, pathogen nucleic acids extracted and separated from shorter cleaved host DNA fragments by, for example, SPRI or electrophoresis and gel purification; this results in a dehosted sequencing library that may, for example, be subjected to unbiased sequencing to identify non-host and/or pathogen nucleic acids that were in the initial human sample. In another embodiment, the recombinant protein can be a methyl-CpG nuclease.

The enzyme treatment may be integrated into modified Illumina library sample preparation workflows to remove host DNA before sequencing. The nuclease can be employed before preparation of the sequencing library. For example, total DNA containing both host and non-host nucleic acids, such as pathogen DNA can be extracted from human plasma. In the case of the histone nuclease or other invention variation where the nuclease recognizes a DNA-binding protein, extraction conditions ensure that any host DNA remains associated with the DNA-binding protein. The recombinant nuclease and any necessary antibodies are added to the mixture. After digestion, all proteins and any other non-DNA molecules are removed, leaving DNA enriched with long fragments from pathogen genomes. These long fragments are then extracted by common size selection methods (e.g., SPRI beads, electrophoresis), leaving short, cleaved host fragments behind. The DNA is then processed by standard library sample preparation methods, e.g., addition of adapters by end-repair and ligation (TRUSEQ®) or transposons (NEXTERA®).

In some embodiments the methods result in a sample or sequencing library that comprises, for example, at least 50%, at least 60%, at least 70%, at least 80%, at least 90%, at least 95%, at least 96%, at least 97%, at least 98%, at least 99%, or 100% non-host nucleic acids, or any range of values thereof. In some embodiments the methods result in a sample or sequencing library in which non-host nucleic acids comprise, for example, from 50% to 100%, from 60% to 100%, from 70% to 100%, from 80% to 100%, from 90% to 100%, or from 95% to 100% of the nucleic acids in the sample or sequencing library. In some embodiments the methods result in a sample or sequencing library that is enriched for non-host nucleic acids. In some embodiments, the sample or sequencing library that is enriched for non-host nucleic acids by 2×, 3×, 4×, 5×, 10×, 20×, 50×, 100×, 200×, 500×, 1000×, 10,000×, 100,000×, or 1,000,000×, compared to the starting sample.

In some embodiments, the library may be amplified using primer sites in the adaptor sequences, and sequenced using sequencing primer sites in the adaptor sequences. In some embodiments the adaptor sequences can include indexes to identify the source of the nucleic acids. The efficiency of subsequent amplification steps can be reduced by the formation of primer-dimers. To increase the efficiency of subsequent amplification steps, non-ligated single-stranded adaptors can be removed from ligation products.

In some embodiments, a ligation-based library preparation method is used (e.g., Illumina TruSeq, Illumina, San Diego Calif.). Ligation-based library preparation methods often make use of an adaptor (e.g., a methylated adaptor) design which can incorporate an index sequence at the initial ligation step and often can be used to prepare samples for single-read sequencing, paired-end sequencing and multiplexed sequencing. For example, nucleic acids (e.g., fragmented nucleic acids or cell-free DNA) may be end repaired by a fill-in reaction, an exonuclease reaction or a combination thereof. In some embodiments the resulting blunt-end repaired nucleic acid can then be extended by a single nucleotide, which is complementary to a single nucleotide overhang on the 3' end of an adapter/primer. Any nucleotide can be used for the extension/overhang nucleotides. In some embodiments nucleic acid library preparation comprises ligating an adapter oligonucleotide. Adapter oligonucleotides are often complementary to flow-cell anchors, and sometimes are utilized to immobilize a nucleic acid library to a solid support, such as the inside surface of a flow cell, for example. In some embodiments, an adapter oligonucleotide comprises an identifier, one or more sequencing primer hybridization sites (e.g., sequences complementary to universal sequencing primers, single end sequencing primers, paired end sequencing primers, multiplexed sequencing primers, and the like), or combinations thereof (e.g., adapter/sequencing, adapter/identifier, adapter/identifier/sequencing).

In some embodiments, a transposon-based library preparation method is used (e.g., NEXTERA®, Epicentre, Madison, Wis.). Transposon-based methods may use in vitro transposition to simultaneously fragment and tag DNA in a single-tube reaction (often allowing incorporation of platform-specific tags and optional barcodes), and prepare sequencer-ready libraries.

In some embodiments a nucleic acid library or parts thereof are amplified (e.g., amplified by a PCR-based method). In some embodiments a sequencing method comprises amplification of a nucleic acid library. A nucleic acid library can be amplified prior to or after immobilization on a solid support (e.g., a solid support in a flow cell). Nucleic acid amplification includes the process of amplifying or increasing the numbers of a nucleic acid template and/or of a complement thereof that are present (e.g., in a nucleic acid library), by producing one or more copies of the template and/or its complement. Amplification can be carried out by any suitable method.

Some embodiments provided herein can include sequencing a nucleic acid. In one embodiment, a sample of mixed nucleic acids is treated with a recombinant protein that cleaves and host DNA while leaving pathogen DNA intact. The pathogen DNA is used to prepare a DNA library, and sequenced. One sequencing methodology is sequencing-by-synthesis (SBS). In SBS, extension of a nucleic acid primer along a nucleic acid template (e.g. a target nucleic acid or amplicon thereof) is monitored to determine the sequence of nucleotides in the template. The underlying chemical process can be polymerization (e.g. as catalyzed by a polymerase enzyme). In a particular polymerase-based SBS embodiment, fluorescently labeled nucleotides are added to a primer (thereby extending the primer) in a template dependent fashion such that detection of the order and type of nucleotides added to the primer can be used to determine the sequence of the template.

One or more amplified encapsulated nucleic acids can be subjected to an SBS or other detection technique that involves repeated delivery of reagents in cycles. For example, to initiate a first SBS cycle, one or more labeled nucleotides, DNA polymerase, etc., can be flowed into/through a hydrogel bead that houses one or more amplified nucleic acid molecules. Those sites where primer extension causes a labeled nucleotide to be incorporated can be detected. Optionally, the nucleotides can further include a reversible termination property that terminates further primer extension once a nucleotide has been added to a primer. For example, a nucleotide analog having a reversible terminator moiety can be added to a primer such that subsequent extension cannot occur until a deblocking agent is delivered to remove the moiety. Thus, for embodiments that use reversible termination, a deblocking reagent can be delivered to the flow cell (before or after detection occurs). Washes can be carried out between the various delivery steps. The cycle can then be repeated n times to extend the primer by n nucleotides, thereby detecting a sequence of length n.

Other sequencing procedures that use cyclic reactions can be used, such as pyrosequencing. Pyrosequencing detects the release of inorganic pyrophosphate (PPi) as particular nucleotides are incorporated into a nascent nucleic acid strand. In pyrosequencing, released PPi can be detected by being immediately converted to adenosine triphosphate (ATP) by ATP sulfurylase, and the level of ATP generated can be detected via luciferase-produced photons. Thus, the sequencing reaction can be monitored via a luminescence detection system. Excitation radiation sources used for fluorescence based detection systems are not necessary for pyrosequencing procedures.

Some embodiments can utilize methods involving the real-time monitoring of DNA polymerase activity. For example, nucleotide incorporations can be detected through fluorescence resonance energy transfer (FRET) interactions between a fluorophore-bearing polymerase and γ-phosphate-labeled nucleotides, or with zero mode waveguides (ZMWs).

Some SBS embodiments include detection of a proton released upon incorporation of a nucleotide into an extension product. For example, sequencing based on detection of released protons can use an electrical detector and associated techniques that are commercially available. Examples of such sequencing systems are pyrosequencing (e.g. commercially available platform from 454 Life Sciences a subsidiary of Roche), sequencing using γ-phosphate-labeled nucleotides (e.g. commercially available platform from Pacific Biosciences) and sequencing using proton detection (e.g. commercially available platform from Ion Torrent subsidiary of Life Technologies).

Another useful sequencing technique is nanopore sequencing. In some nanopore embodiments, the target nucleic acid or individual nucleotides removed from a target nucleic acid pass through a nanopore. As the nucleic acid or nucleotide passes through the nanopore, each nucleotide type can be identified by measuring fluctuations in the electrical conductance of the pore.

In methods of isolating nucleic acids, amplification, and sequencing, various reagents may be used for nucleic acid isolation and preparation. Such reagents may include, for example, lysozyme, proteinase K, random hexamers, polymerase (for example, Φ29 DNA polymerase, Taq polymerase, Bsu polymerase), transposase (for example, Tn5), primers (for example, P5 and P7 adaptor sequences), ligase, catalyzing enzyme, deoxynucleotide triphosphates, buffers, or divalent cations.

Adaptors can include sequencing primer sites, amplification primer sites, and indexes. As used herein an "index" can include a sequence of nucleotides that can be used as a molecular identifier and/or barcode to tag a nucleic acid, and/or to identify the source of a nucleic acid. In some embodiments, an index can be used to identify a single nucleic acid, or a subpopulation of nucleic acids. In some embodiments, nucleic acid libraries can be prepared within a hydrogel on a flow cell device.

Kits

Some embodiments provided herein relate to a kit for removing host DNA from a sample comprising host DNA and non-host nucleic acids, the kit comprising: (a) any of the recombinant proteins described above; and (b) a reagent selected from the group consisting of: an antibody that selectively binds to a DNA-binding protein or to methylated CpG, a second recombinant protein comprising a second nuclease domain, a reagent for removing cleaved host DNA from non-host DNA, a library preparation reagent, and a nucleic acid sequencing reagent. In some embodiments, the DNA-binding protein is a chromatin protein, such as a histone. For example, the kit may include a recombinant histone nuclease and a reagent for removing cleaved host DNA from non-host DNA, or a methyl-CpG nuclease and a library preparation reagent.

As used herein, the term "reagent" describes an agent or a mixture of two or more agents useful for reacting with, interacting with, diluting, or adding to a sample. Examples of library preparation reagents and nucleic acid sequencing reagents include agents used in nucleic acid amplification reactions, including, for example buffers, chemicals, enzymes, template nucleic acids, nucleotides, labels, dyes, nucleases, random hexamers, polymerase (for example, Φ29 DNA polymerase, Taq polymerase, Bsu polymerase), a primer, catalyzing enzyme, deoxynucleotide triphosphates, buffers, and divalent cations. In some embodiments, the library preparation reagent can include a transposase such as Tn5, an adaptor sequence, or a ligase. Examples of reagents for removing cleaved host DNA from non-host DNA include buffers, ethanol, isopropanol, agarose, and other gelling agents.

EXAMPLES

Example 1—Recombinant Nucleases

Genes encoding the recombinant proteins were each synthesized, expressed in *E. coli* BL21 AI, and the expressed proteins were purified. Recombinant proteins included: (1) PGFkShHomo1 which included a Protein G-binding domain, a FokI nuclease, and a homodimer-binding domain; (2) MBwtFkShKKR1 which included a wild-type MBD2-binding domain, a FokI nuclease domain, and a KKR heterodimer domain; and (3) MBmuFkShELD1 which included an enhanced mutant MBD2-binding domain, a FoId nuclease domain, and an ELD heterodimer domain. FokI nuclease domains included Sharkey mutations of SEQ ID NO:10.

Figure 9:
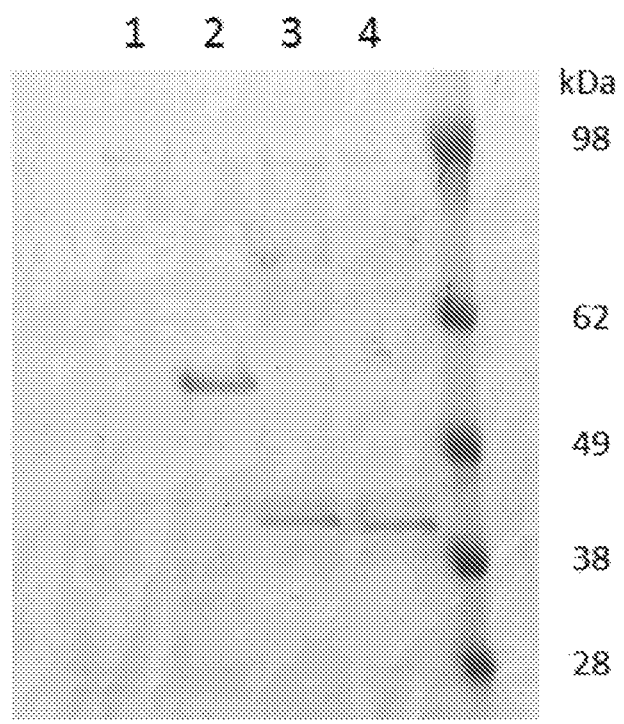
FIG. 9 is a photograph of a Coomassie blue-stained polyacrylamide gel that was loaded with purified recombinant proteins. Lane 1 was loaded with a negative control from BL21 AI *E. coli* that was not transformed with DNA encoding a recombinant dehosting protein. Lanes 2-4 were loaded with purified recombinant proteins expressed from PGFkShHomo1, MBmuFkShELD1, and MBwtFkShKKR1 DNA constructs, respectively, in BL21 AI *E. coli*.

FIG. 9 shows a Coomassie blue-stained polyacrylamide gel loaded with the purified recombinant proteins. In FIG. 9, lane 1 is a negative control, lanes 2-4 are the purified recombinant proteins. The bands in the gel confirmed that the recombinant nucleases were expressed.

Figure 10:
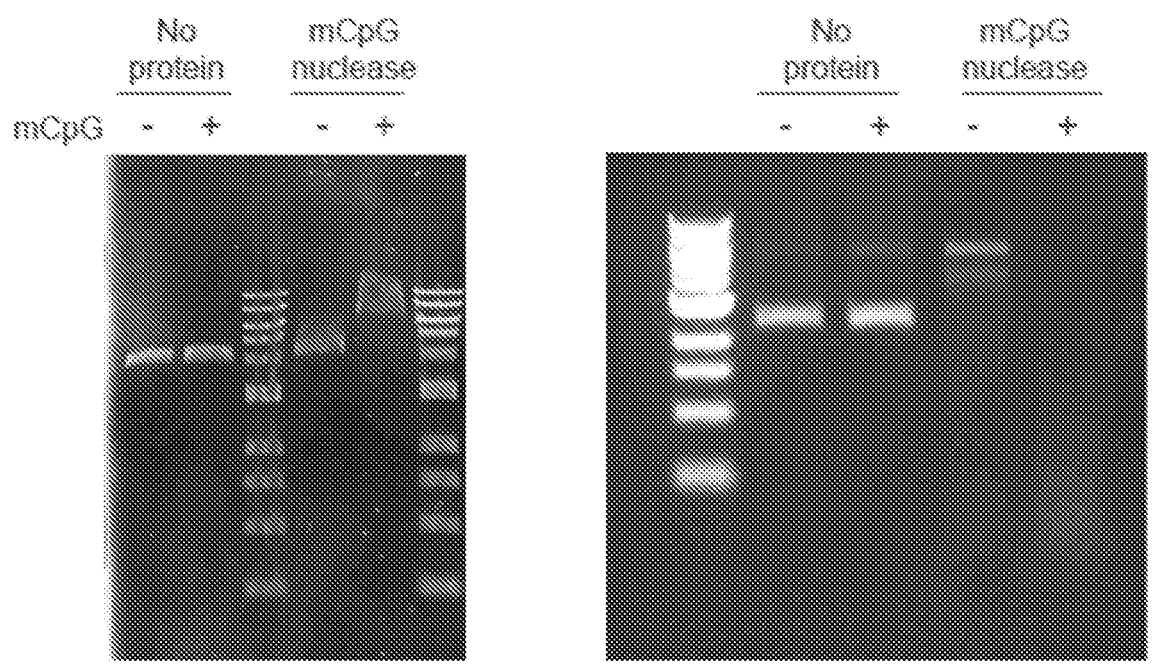
FIG. 10 (left and right panels) are photographs of ethidium bromide-stained nucleic acids in agarose gels. The gel in the left panel was loaded with methyl-CpG DNA or non-methyl-CpG DNA, combined with or without purified a recombinant methylated CpG nuclease (mCpGnuclease). The gel in the right panel was loaded with methyl-CpG DNA or non-methyl-CpG DNA, combined with or without a purified mCpGnuclease, or with a negative control.

A recombinant methylated CpG nuclease (mCpG nuclease) which included the DNA binding domains from MBD2 and the nuclease domain from FokI Sharkey was synthesized, expressed, and purified. To demonstrate selective binding of the mCpG nuclease to methylated CpG DNA, the mCpG nuclease was incubated with either methylated CpG DNA or non-methylated CpG DNA, and the complexes resolved on an agarose gel. FIG. 10 (left panel) shows a band shift for the mCpG nuclease incubated with methylated CpG DNA (+), compared to the mCpG nuclease incubated with non-methylated CpG DNA (−). Thus, the mCpG nuclease selectively bound to methylated CpG DNA. To demonstrate nuclease activity of the mCpG nuclease for methylated CpG DNA, the mCpG nuclease was incubated with supercoiled plasmid DNA comprising either methylated CpG DNA (+) or non-methylated CpG DNA (−), and the products were resolved on an agarose gel. FIG. 10 (right panel) shows that mCpG nuclease selectively digested supercoiled plasmid DNA comprising methylated CpG DNA.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A composition comprising:
   (a) a recombinant protein comprising: a binding domain that selectively binds to a DNA-binding protein, to a methylated CpG, or to an antibody; and a nuclease domain; and
   (b) a mixture comprising: (i) host DNA bound to the DNA-binding protein and comprising the methylated CpG; and (ii) non-host nucleic acids not bound to the DNA-binding protein and lacking the methylated CpG.

2. The composition of claim 1, wherein the binding domain comprises a binding domain of a protein selected from the group consisting of retinoblastoma binding protein 4 (RBBP4), methyl-CpG binding domain protein 2 (MECP2), methyl-CpG binding domain protein 1 (MBD1), methyl-CpG binding domain protein 2 (MBD2), or methyl-CpG binding domain protein 4 (MBD4), Protein G, and Protein A; and wherein the nuclease domain comprises a nuclease domain of a protein selected from FokI, TevI, and functional fragments thereof.

3. The composition of claim 2, wherein the recombinant protein comprises a linker between the binding domain and the nuclease domain.

4. The composition of claim 2, wherein the binding domain comprises a binding domain of Protein G or MBD2.

5. The composition of claim 4, wherein the binding domain comprises the binding domain of Protein G, and the composition further comprises an antibody or antigen binding fragment thereof capable of binding to a histone or 5-methylcytosine.

6. The composition of claim 4, wherein the binding domain comprises the binding domain of MBD2.

7. The composition of claim 2, wherein the nuclease domain comprises a homodimer.

8. The composition of claim 2, wherein the nuclease domain comprises a heterodimer.

9. The composition of claim 2, wherein the nuclease domain comprises a nuclease domain of a FokI Sharkey variant, a FokI KKR variant, or a FokI ELD variant.

10. The composition of claim 2, wherein the nuclease domain comprises a polypeptide having at least 95% sequence identity with the amino acid sequence of any one of SEQ ID NOs:01-11.

11. The composition of claim 2, wherein the nuclease domain comprises a polypeptide having at least 95% sequence identity with the amino acid sequence of any one of SEQ ID NO:08, SEQ ID NO:09, or SEQ ID NO:10.

12. The composition of claim 2, comprising: a binding domain of Protein G and a nuclease domain of a FokI Sharkey variant; a binding domain of MBD2 and a nuclease domain of a FokI Sharkey variant and of a FokI KKR1 variant; or a binding domain of MBD2 and a nuclease domain of a FokI Sharkey variant and of a FokI ELD1 variant.

13. The composition of claim 1, wherein the DNA binding protein is a histone, the host DNA is human genomic DNA, and the non-host nucleic acids are prokaryotic nucleic acids or viral nucleic acids.

14. The composition of claim 1, further comprising a substrate adapted to remove cleaved host DNA from non-host nucleic acids.

15. The composition of claim 14, wherein the substrate comprises a plurality of solid phase reversible immobilization (SPRI) beads.

16. The composition of claim 1, further comprising a gel adapted to remove cleaved host DNA from non-host nucleic acids by gel filtration or gel electrophoresis.

17. The composition of claim 1, further comprising a protease adapted to remove the recombinant protein from cleaved host DNA and non-host nucleic acids.

18. The composition of claim 1, further comprising a reagent adapted to precipitate nucleic acids selected from ethanol and isopropanol.

* * * * *

UNITED STATES PATENT AND TRADEMARK OFFICE
CERTIFICATE OF CORRECTION

| | |
|---|---|
| PATENT NO. | : 11,773,427 B2 |
| APPLICATION NO. | : 16/609705 |
| DATED | : October 3, 2023 |
| INVENTOR(S) | : Wang |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 269 days.

Signed and Sealed this
Eighth Day of July, 2025

Coke Morgan Stewart
*Acting Director of the United States Patent and Trademark Office*

SEQUENCE LISTING

```
<160> NUMBER OF SEQ ID NOS: 11

<210> SEQ ID NO 1
<211> LENGTH: 196
<212> TYPE: PRT
<213> ORGANISM: Artificial Sequence
<220> FEATURE:
<223> OTHER INFORMATION: FokI variant, Wild-Type
```

<400> SEQUENCE: 1

```
Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195
```

<210> SEQ ID NO 2
<211> LENGTH: 196
<212> TYPE: PRT
<213> ORGANISM: Artificial Sequence
<220> FEATURE:
<223> OTHER INFORMATION: FokI variant EL

<400> SEQUENCE: 2

```
Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110

Asn Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140
```

```
Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
                180                 185                 190

Glu Ile Asn Phe
            195

<210> SEQ ID NO 3
<211> LENGTH: 196
<212> TYPE: PRT
<213> ORGANISM: Artificial Sequence
<220> FEATURE:
<223> OTHER INFORMATION: FokI variant KK

<400> SEQUENCE: 3

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
                180                 185                 190

Glu Ile Asn Phe
            195

<210> SEQ ID NO 4
<211> LENGTH: 196
<212> TYPE: PRT
<213> ORGANISM: Artificial Sequence
<220> FEATURE:
<223> OTHER INFORMATION: FokI variant D

<400> SEQUENCE: 4

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45
```

```
Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Pro Ile
                 85                  90                  95

Gly Gln Ala Asp Glu Met Gln Asp Tyr Val Glu Glu Asn Gln Thr Arg
                100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
                180                 185                 190

Glu Ile Asn Phe
            195

<210> SEQ ID NO 5
<211> LENGTH: 196
<212> TYPE: PRT
<213> ORGANISM: Artificial Sequence
<220> FEATURE:
<223> OTHER INFORMATION: FokI variant R

<400> SEQUENCE: 5

Gln Leu Val Lys Ser Glu Leu Glu Glu Lys Lys Ser Glu Leu Arg His
  1               5                  10                  15

Lys Leu Lys Tyr Val Pro His Glu Tyr Ile Glu Leu Ile Glu Ile Ala
                 20                  25                  30

Arg Asn Ser Thr Gln Asp Arg Ile Leu Glu Met Lys Val Met Glu Phe
             35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
 65                  70                  75                  80

Val Ile Val Asp Thr Lys Ala Tyr Ser Gly Gly Tyr Asn Leu Pro Ile
                 85                  90                  95

Gly Gln Ala Arg Glu Met Gln Arg Tyr Val Glu Glu Asn Gln Thr Arg
                100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
                180                 185                 190

Glu Ile Asn Phe
            195
```

```
<210> SEQ ID NO 6
<211> LENGTH: 196
<212> TYPE: PRT
<213> ORGANISM: Artificial Sequence
<220> FEATURE:
<223> OTHER INFORMATION: FokI variant EA

<400> SEQUENCE: 6

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Asn Gln Thr Arg
            100                 105                 110

Asn Lys His Ala Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195

<210> SEQ ID NO 7
<211> LENGTH: 196
<212> TYPE: PRT
<213> ORGANISM: Artificial Sequence
<220> FEATURE:
<223> OTHER INFORMATION: FokI variant KV

<400> SEQUENCE: 7

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
```

```
                  100                 105                 110
Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
        130                 135                 140

Tyr Lys Ala Gln Leu Thr Arg Leu Asn His Val Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195
```

```
<210> SEQ ID NO 8
<211> LENGTH: 196
<212> TYPE: PRT
<213> ORGANISM: Artificial Sequence
<220> FEATURE:
<223> OTHER INFORMATION: FokI variant ELD

<400> SEQUENCE: 8
```

```
Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110

Asp Lys His Leu Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
            195
```

```
<210> SEQ ID NO 9
<211> LENGTH: 196
<212> TYPE: PRT
<213> ORGANISM: Artificial Sequence
<220> FEATURE:
<223> OTHER INFORMATION: FokI variant KKR

<400> SEQUENCE: 9
```

Gln Leu Val Lys Ser Glu Leu Glu Glu Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn Arg Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 10
<211> LENGTH: 196
<212> TYPE: PRT
<213> ORGANISM: Artificial Sequence
<220> FEATURE:
<223> OTHER INFORMATION: FokI variant Sharkey

<400> SEQUENCE: 10

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Pro Thr Gln Asp Arg Ile Leu Glu Met Lys Val Met Glu Phe
            35                  40                  45

Phe Met Lys Val Tyr Gly Tyr Arg Gly Glu His Leu Gly Gly Ser Arg
        50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

```
Ala Val Leu Ser Val Glu Glu Leu Leu Ile Gly Gly Glu Met Ile Lys
            165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 11
<211> LENGTH: 196
<212> TYPE: PRT
<213> ORGANISM: Artificial Sequence
<220> FEATURE:
<223> OTHER INFORMATION: FokI variant Sharkey'

<400> SEQUENCE: 11

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Pro Thr Gln Asp Arg Ile Leu Glu Met Lys Val Met Glu Phe
        35                  40                  45

Leu Met Lys Val Tyr Gly Tyr Arg Gly Glu His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly His Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly Tyr Phe Lys Gly Asp
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Gln
            165                 170                 175

Ala Gly Thr Leu Thr Leu Glu Glu Val Arg Arg Lys Phe Asn Asn Gly
            180                 185                 190

Glu Ile Asn Phe
        195
```